United States Patent
Salganicoff et al.

(10) Patent No.: US 11,037,070 B2
(45) Date of Patent: Jun. 15, 2021

(54) DIAGNOSTIC TEST PLANNING USING MACHINE LEARNING TECHNIQUES

(71) Applicant: Siemens Healthcare GmbH, Erlangen (DE)

(72) Inventors: Marcos Salganicoff, Bala Cynwyd, PA (US); Xiang Sean Zhou, Exton, PA (US); Gerardo Hermosillo Valadez, West Chester, PA (US); Luca Bogoni, Philadelphia, PA (US)

(73) Assignee: Siemens Healthcare GmbH, Erlangen (DE)

(*) Notice: Subject to any disclaimer, the term of this patent is extended or adjusted under 35 U.S.C. 154(b) by 966 days.

(21) Appl. No.: 15/134,543

(22) Filed: Apr. 21, 2016

(65) Prior Publication Data

US 2016/0321414 A1    Nov. 3, 2016

Related U.S. Application Data

(60) Provisional application No. 62/154,394, filed on Apr. 29, 2015.

(51) Int. Cl.
*G06N 20/00*     (2019.01)
*G06N 5/00*      (2006.01)
*G16H 50/20*     (2018.01)

(52) U.S. Cl.
CPC .............. *G06N 20/00* (2019.01); *G06N 5/003* (2013.01); *G16H 50/20* (2018.01)

(58) Field of Classification Search
CPC .... G06F 17/00; G06F 17/30; G06F 17/30528; G06F 19/00; G06F 19/24; G06F 19/28; G06F 19/322; G06F 19/3431; G06F 19/345; G06N 5/02; G06N 99/00; G06N 99/005
See application file for complete search history.

(56) References Cited

U.S. PATENT DOCUMENTS

| | | | | |
|---|---|---|---|---|
| 5,214,577 A | * | 5/1993 | Sztipanovits | ...... G05B 23/0262 700/79 |
| 6,007,231 A | * | 12/1999 | Vijg | ...... C12Q 1/686 435/91.1 |
| 6,338,148 B1 | * | 1/2002 | Gillenwater | ...... G06F 11/2273 714/25 |

(Continued)

OTHER PUBLICATIONS

Chang, H.Y. et al. (1965). "An Algorithm for Selecting an Optimum Set of Diagnostic Tests". IEEE Transactions on Electronic Computers vol. EC-14, No. 5 Oct. 1965. pp. 706-711. (Year: 1965).*

(Continued)

*Primary Examiner* — Kamran Afshar
*Assistant Examiner* — Benjamin J Buss

(57) ABSTRACT

A framework diagnostic test planning is described herein. In accordance with one aspect, the framework receives data representing one or more sample patients, diagnostic tests administered to the one or more sample patients, diagnostic test results and confirmed medical conditions associated with the administered diagnostic tests. The framework trains one or more classifiers based on the data to identify diagnostic test plans from the diagnostic tests. The one or more classifiers may then be applied to current patient data to generate a diagnostic test plan for a given patient.

20 Claims, 3 Drawing Sheets

(56) References Cited

U.S. PATENT DOCUMENTS

| | | | | |
|---|---|---|---|---|
| 6,532,305 B1* | 3/2003 | Hammen | | G06K 9/6282 |
| | | | | 382/159 |
| 7,958,407 B2* | 6/2011 | Underdal | | G06N 5/02 |
| | | | | 714/57 |
| 8,423,226 B2* | 4/2013 | Underdal | | G06N 7/005 |
| | | | | 701/31.4 |
| 8,428,813 B2* | 4/2013 | Gilbert | | G06N 5/04 |
| | | | | 701/31.4 |
| 9,081,883 B2* | 7/2015 | Wittliff, III | | G16H 50/20 |
| 9,141,756 B1* | 9/2015 | Hillis | | G06F 19/12 |
| 10,032,526 B2* | 7/2018 | Lynn | | G16H 10/60 |
| 2001/0023419 A1* | 9/2001 | Lapointe | | G06F 19/00 |
| | | | | 706/15 |
| 2002/0087499 A1* | 7/2002 | Stockfisch | | G06N 5/025 |
| | | | | 706/59 |
| 2004/0015337 A1* | 1/2004 | Thomas | | G16H 50/20 |
| | | | | 703/11 |
| 2004/0186816 A1* | 9/2004 | Lienhart | | G06N 20/00 |
| | | | | 706/20 |
| 2005/0020903 A1* | 1/2005 | Krishnan | | G16H 50/20 |
| | | | | 600/407 |
| 2005/0059876 A1* | 3/2005 | Krishnan | | G06T 7/0012 |
| | | | | 600/407 |
| 2006/0063156 A1* | 3/2006 | Willman | | C12Q 1/6886 |
| | | | | 435/6.14 |
| 2006/0122465 A1* | 6/2006 | Bastien | | G16H 50/20 |
| | | | | 600/300 |
| 2006/0184475 A1* | 8/2006 | Krishnan | | G16H 50/20 |
| | | | | 706/20 |
| 2007/0037144 A1* | 2/2007 | Wohlgemuth | | C12Q 1/6837 |
| | | | | 435/6.12 |
| 2007/0168225 A1* | 7/2007 | Haider | | G06F 19/3481 |
| | | | | 705/2 |
| 2007/0293998 A1* | 12/2007 | Underdal | | G06N 5/02 |
| | | | | 701/31.4 |
| 2008/0057590 A1* | 3/2008 | Urdea | | G06Q 50/24 |
| | | | | 705/3 |
| 2008/0086272 A1* | 4/2008 | Fillet | | G16B 20/00 |
| | | | | 702/19 |
| 2008/0221927 A1* | 9/2008 | Levy | | G06Q 50/24 |
| | | | | 705/3 |
| 2008/0284582 A1* | 11/2008 | Wang | | A61B 5/0205 |
| | | | | 340/521 |
| 2008/0313223 A1* | 12/2008 | Miller | | G06N 5/04 |
| 2009/0092299 A1* | 4/2009 | Jerebko | | G06K 9/622 |
| | | | | 382/128 |
| 2009/0136139 A1* | 5/2009 | Kataoka | | G06K 9/00503 |
| | | | | 382/207 |
| 2009/0319244 A1* | 12/2009 | West | | G06K 9/6282 |
| | | | | 703/11 |
| 2010/0063410 A1* | 3/2010 | Avila | | A61B 5/08 |
| | | | | 600/532 |
| 2010/0131434 A1* | 5/2010 | Magent | | G06Q 10/06 |
| | | | | 706/11 |
| 2010/0143956 A1* | 6/2010 | Maurer | | G01N 33/5014 |
| | | | | 435/15 |
| 2010/0174555 A1* | 7/2010 | Abraham-Fuchs | | G06F 19/328 |
| | | | | 705/3 |
| 2010/0257027 A1* | 10/2010 | Greenberg | | G06Q 10/10 |
| | | | | 705/7.29 |
| 2011/0161104 A1* | 6/2011 | Gilbert | | G06N 5/003 |
| | | | | 705/2 |
| 2011/0230372 A1* | 9/2011 | Willman | | C12Q 1/6886 |
| | | | | 506/16 |
| 2012/0030779 A1* | 2/2012 | Benjamin | | A01K 67/0275 |
| | | | | 800/9 |
| 2012/0077695 A1* | 3/2012 | Ostroff | | C12Q 1/6886 |
| | | | | 506/9 |
| 2012/0209625 A1* | 8/2012 | Armstrong | | G06F 19/326 |
| | | | | 705/3 |
| 2012/0282648 A1* | 11/2012 | Simon | | G01N 33/57434 |
| | | | | 435/29 |
| 2012/0317127 A1* | 12/2012 | Friedlander | | G06Q 50/22 |
| | | | | 707/752 |
| 2013/0004044 A1* | 1/2013 | Ross | | G06T 7/0016 |
| | | | | 382/131 |
| 2013/0066199 A1* | 3/2013 | Ramanujan | | G01N 21/6458 |
| | | | | 600/431 |
| 2013/0080379 A1* | 3/2013 | Stergiou | | G16H 40/40 |
| | | | | 706/55 |
| 2013/0080836 A1* | 3/2013 | Stergiou | | G16H 50/20 |
| | | | | 714/37 |
| 2013/0225439 A1* | 8/2013 | Princen | | C12Q 1/6883 |
| | | | | 506/9 |
| 2013/0275350 A1* | 10/2013 | Schaffer | | G06F 19/00 |
| | | | | 705/3 |
| 2013/0304494 A1* | 11/2013 | Friedlander | | G06F 19/321 |
| | | | | 705/2 |
| 2014/0186366 A1* | 7/2014 | Seva | | G01N 33/57419 |
| | | | | 424/158.1 |
| 2014/0199273 A1* | 7/2014 | Cesano | | G01N 33/57426 |
| | | | | 424/93.7 |
| 2014/0279746 A1* | 9/2014 | De Bruin | | G16H 20/70 |
| | | | | 706/12 |
| 2015/0081324 A1* | 3/2015 | Adjaoute | | G06Q 40/08 |
| | | | | 705/2 |
| 2015/0164359 A1* | 6/2015 | Amirim | | G06F 19/00 |
| 2015/0193583 A1* | 7/2015 | McNair | | G16H 50/20 |
| | | | | 705/2 |
| 2016/0012193 A1* | 1/2016 | Almogy | | G06F 19/00 |
| | | | | 705/3 |
| 2016/0203263 A1* | 7/2016 | Maier | | G06F 19/321 |
| | | | | 705/2 |
| 2016/0217133 A1* | 7/2016 | Reiter | | G08B 5/22 |
| 2016/0267235 A1* | 9/2016 | Draghici | | G06F 19/00 |
| 2016/0349271 A1* | 12/2016 | Zhuo | | G01N 33/6893 |
| 2016/0376652 A1* | 12/2016 | Sarwal | | C12Q 1/6883 |
| | | | | 514/789 |
| 2017/0046839 A1* | 2/2017 | Paik | | G06K 9/6296 |
| 2017/0340262 A1* | 11/2017 | Momose | | A61B 10/00 |
| 2019/0096526 A1* | 3/2019 | Hirsch | | G16H 50/70 |

OTHER PUBLICATIONS

Kukar, M. (Jul. 2001). "Making reliable diagnoses with machine learning: A case study". In Conference on Artificial Intelligence in Medicine in Europe (pp. 88-98). Springer, Berlin, Heidelberg. (Year: 2001).*

Thompson, M.L. (2003). "Assessing the diagnostic accuracy of a sequence of tests". Biostatistics, 4(3), 341-351. (Year: 2003).*

Kahn, K.S. et al. (2003). "Systematic reviews with individual patient data meta-analysis to evaluate diagnostic tests". European Journal of Obstetrics & Gynecology and Reproductive Biology, 108(2), 121-125. DOI:10.1016/S0301-2115(03)00098-8 (Year: 2003).*

Kukar, M. (2003). "Transductive reliability estimation for medical diagnosis". Artificial Intelligence in Medicine, 29(1-2), 81-106. (Year: 2003).*

BOSSUYT, P.M. et al. (2006). "Comparative accuracy: assessing new tests against existing diagnostic pathways". Bmj, 332(7549), 1089-1092. DOI:10.1136/bmj.332.7549.1089 (Year: 2006).*

Mehrotra, K.G. et al. (2007). "Squeezing the last drop: Cluster-based classification algorithm". Statistics & probability letters, 77(12), 1288-1299. DOI:10.1016/j.spl.2007.03.014 (Year: 2007).*

Ramirez, J. et al. (2009). "Computer aided diagnosis of the Alzheimer's Disease combining SPECT-based feature selection and Random forest classifiers". 2009 IEEE Nuclear Science Symposium Conference Record. IEEE. pp. 2738-2742. (Year: 2009).*

Adidela, D.R. et al. (2012). "Application of Fuzzy ID3 to Predict Diabetes". International Journal of Advanced Computer and Mathematical Sciences, ISSN 2230-9624. vol. 3, Issue 4, 2012, pp. 541-545. DOI:10.17485/ijst/2015/v8i8/69272 (Year: 2012).*

Lavanya, D. et al. (2012). "Ensemble Decision Tree Classifier for Breast Cancer Data". International Journal of Information Technology Convergence and Services (IJITCS) vol. 2, No. 1, Feb. 2012. (Year: 2012).*

(56) References Cited

OTHER PUBLICATIONS

Mporas, I. et al. (Aug. 21, 2015). "Sleep Stages Classification from Electroencephalographic Signals Based on Unsupervised Feature Space Clustering". In International Conference on Brain Informatics and Health (pp. 77-85). Springer, Cham. (Year: 2015).*

Nagarajan, S. et al. (2015). "Design and implementation of expert clinical system for diagnosing diabetes using data mining techniques". Indian Journal of science and Technology, 8(8), 771-776. (Year: 2015).*

Jin, H. et al. (2008). "A Procedure for Determining Whether a Simple Combination of Diagnostic Tests May Be Noninferior to the Theoretical Optimum Combination". Medical Decision Making/ Nov.-Dec. 2008. pp. 909-916. (Year: 2008).*

Ling, C.X. et al. (2006). "Test strategies for cost-sensitive decision trees." IEEE Transactions on Knowledge and Data Engineering 18.8 (2006): 1055-1067. (Year: 2006).*

\* cited by examiner

DIAGNOSTIC TEST PLANNING USING MACHINE LEARNING TECHNIQUES

CROSS-REFERENCE TO RELATED APPLICATION

The present application claims the benefit of U.S. provisional application No. 62/154,394 filed Apr. 29, 2015, the entire contents of which are herein incorporated by reference.

TECHNICAL FIELD

The present disclosure generally relates to data processing, and more particularly to diagnostic test planning.

BACKGROUND

A diagnostic test is a medical test performed to facilitate diagnosis or detection of disease, injury or any other medical condition. Some diagnostic tests are designed as part of a physical examination that can be performed by simple tools in a medical office environment using point-of-care diagnostic equipment, while other tests may require elaborate equipment or the use of a sterile operating theatre environment. Some tests require biological samples to be analyzed in a laboratory, while other tests may be performed using simple chemical tests in the clinic.

New monolithic diagnostic tests are typically developed in an interactive manner based on specific medical and biological operating principles and mechanisms. The development process may begin with the generation of prototype tests, associated experimental design and hypothesis testing, followed by refinement cycles of the prior steps, and concluding with transfer of design for manufacturing and obtaining regulatory approvals as required.

Diagnostic tests are typically developed to target a specific disease or condition. However, many possible medical conditions or diseases may affect a patient. It may be too costly, time-prohibitive or impractical to apply all tests for all potential medical conditions or diseases.

SUMMARY

Described herein are systems and methods for planning diagnostic tests. In accordance with one aspect, the framework receives data representing one or more sample patients, diagnostic tests administered to the one or more sample patients, diagnostic test results and confirmed medical conditions associated with the administered diagnostic tests. The framework trains one or more classifiers based on the data to identify diagnostic test plans. The one or more classifiers may then be applied to current patient data to generate a diagnostic test plan for a given patient. The diagnostic test plan may include a composite diagnostic test sequence. A diagnosis may be determined based on results of the diagnostic tests in the diagnostic test plan.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
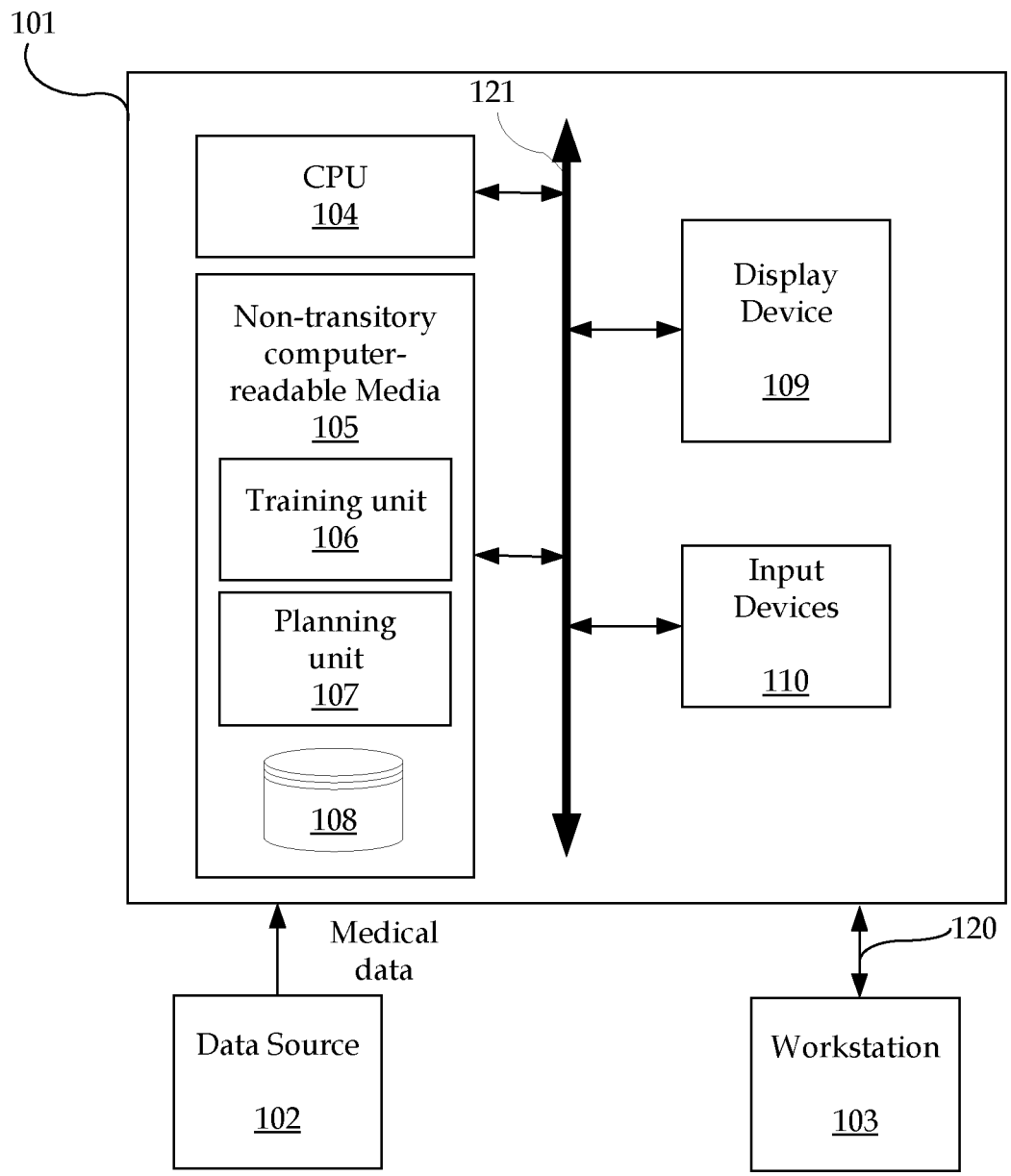
FIG. 1 is a block diagram illustrating an exemplary system.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

A framework for planning diagnostic tests is described herein. In accordance with one aspect, diagnostic test plans are developed based on retrospective data of groups of patients. In some implementations, the framework stores data associated with potential diagnostic tests and confirmed outcomes (e.g., medical conditions, risk levels) for a given patient population in a database. Such data may then be used by machine learning techniques to cluster patients and diagnostic tests into meaningful sets to maximize diagnostic accuracy, while minimizing the number of required tests. The diagnostic tests may be combined in a diagnostic test plan that includes sequence chains and/or parallel combinations of monolithic tests. Regression or machine learning techniques may be used to train classifiers (or predictive functions) to identify subsets of diagnostic tests or diagnostic test plans. These and other exemplary features and advantages will be described herein in more detail.

FIG. 1 is a block diagram illustrating an exemplary system 100. The system 100 includes a computer system 101 for implementing the framework as described herein. In some implementations, computer system 101 operates as a standalone device. In other implementations, computer system 101 may be connected (e.g., using a network) to other machines, such as user device 103. In a networked deployment, computer system 101 may operate in the capacity of a server (e.g., thin-client server, such as syngo.via® by Siemens Healthcare), a cloud computing platform, a client user machine in server-client user network environment, or as a peer machine in a peer-to-peer (or distributed) network environment.

In one implementation, computer system 101 comprises a processor or central processing unit (CPU) 104 coupled to one or more non-transitory computer-readable media 105 (e.g., computer storage or memory), display device 109 (e.g., monitor) and various input devices 110 (e.g., mouse or keyboard) via an input-output interface 121. Computer system 101 may further include support circuits such as a cache, a power supply, clock circuits and a communication bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein are implemented as computer-readable program code tangibly embodied in non-transitory computer-readable media 105. In particular, the present techniques may be implemented by training unit 106 and planning unit 107. Non-transitory computer-readable media 105 may include random access memory (RAM), read-only memory (ROM), magnetic floppy disk, flash memory, and other types of memories, or a combination thereof. The computer-readable program code is executed by CPU 104 to process data. As such, the computer system 101 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 105 may be used for storing a database (or dataset) 108. Such data may also be stored in external storage or other memories. The external storage may be implemented using a database management system (DBMS) managed by the CPU 104 and residing on a memory, such as a hard disk, RAM, or removable media. The external storage may be implemented on one or more additional computer systems. For example, the external storage may include a data warehouse system residing on a separate computer system, a picture archiving and communication system (PACS), or any other now known or later developed hospital, medical institution, medical office, testing facility, pharmacy or other medical patient record storage system.

The data source 102 may provide training data for processing by training unit 106. Such data may include, for example, data associated with patients, diagnostic tests and respective confirmed conditions. Such data may also be stored in database 108. Data source 102 may be a computer, memory device, a radiology scanner (e.g., X-ray or a CT scanner), laboratory or point-of-care in-vitro diagnostic (IVD) equipment (e.g. Blood Panel Analyzer, Molecular Diagnostic Analyzer or Sequencer) and/or appropriate peripherals (e.g., keyboard and display device) for acquiring, inputting, collecting, generating and/or storing such data.

User device 103 may include a computer (e.g., mobile computing device) and appropriate peripherals, such as a keyboard and display device, and can be operated in conjunction with the entire system 100. User device 103 may include a graphical user interface to collect current patient data 120. User input may be received via an input device (e.g., keyboard, mouse, touch screen voice or video recognition interface, etc.).

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2:
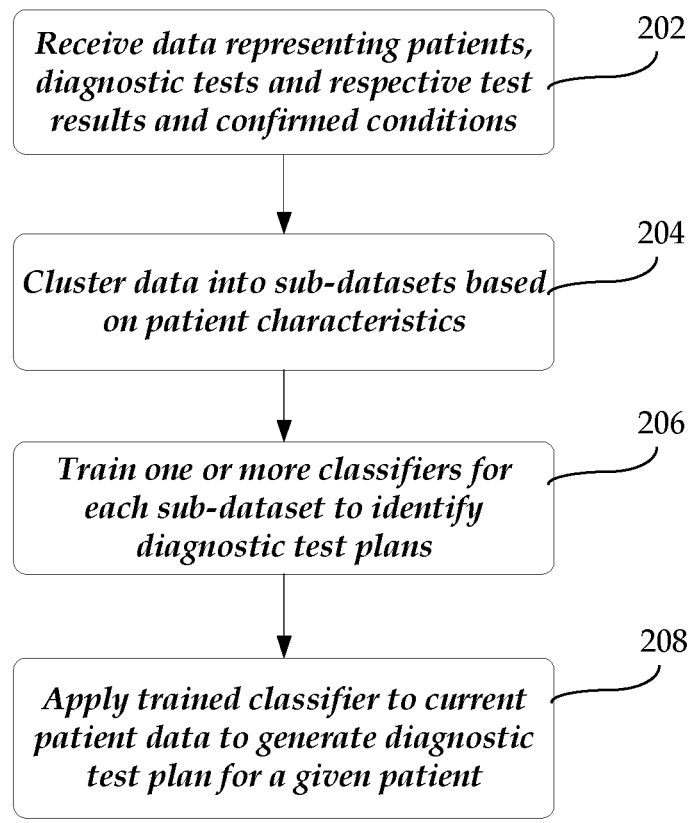
FIG. 2 shows an exemplary method of generating a diagnostic test plan.

FIG. 2 shows an exemplary method 200 of generating a diagnostic test plan by a computer system. It should be understood that the steps of the method 200 may be performed in the order shown or a different order. Additional, different, or fewer steps may also be provided. Further, the method 200 may be implemented with the system 101 of FIG. 1, a different system, or a combination thereof.

At 202, training unit 106 receives data representing one or more sample patients P, diagnostic tests D, respective test results R and confirmed medical conditions C. The data may further include other information associated with the sample patients P, such as patient records or information derived therefrom (e.g., preexisting medical conditions, demographic attributes, physical attributes, family history, habits, preexisting medical conditions, temporary symptoms, patient management history, therapy outcomes). Information (e.g., known risks, complications or side-effects typically associated with certain therapies, therapy costs) from other data sources, such as published literature or peer-reviewed journals, may also be received. Such data may be stored or hosted in database 108.

The set of diagnostic tests $D=\{d_i|i=1, n\}$ may be administered to the set of one or more sample patients $P=\{p_j|j=1, m\}$ to yield test results $R=\{r_{i,j,k,l}|\forall\ i, j, k, l\}$. Each test result $r_{i,j,k,l}$ may be binary, categorical or real-valued. The administered diagnostic tests D and test results R may further be associated with post-hoc confirmation of outcomes $C=\{c_{j,k,l}|\forall\ j, k, l\}$. The outcomes C indicate the presence or absence of a medical condition, complication, risk or disease (e.g., cancer). The outcomes C may be confirmed by a specialist or medical personnel in a definitive test to form the "ground truth" for comparing with the test results. This confirmation may be performed shortly after the diagnostic tests have been administered to the patients, or may be performed later in the patient history and used retrospectively. The set of outcomes C may also include the associated risk levels, as well as those outcomes that may have been overlooked earlier in the patient treatment, and those that were detected by a dedicated diagnostic test at the appropriate time.

The set of diagnostic tests D may be applied longitudinally to the same sample patient over time. Alternatively, the set of potential diagnostic tests D may be applied across the whole sample patient population based on many image data from various sample patients (e.g., in the order of thousands). Not all sample patients $p_j$ may receive the same set of diagnostic tests. The diagnostic tests may be administered contemporaneously or at different times, over a given time span, each occurring at a time $t_l$. The results from a diagnostic test administered at time $t_m$ for disease $c_k$ may be denoted by $r_{i,j,k,l}$. Any given diagnostic test in D may yield a test result that is binary, categorical or real-valued (e.g. r).

Any type of diagnostic tests $d_i$ may be applied. Such diagnostic tests may be invasive, minimally invasive or non-invasive. In some implementations, the diagnostic tests include automated or manual measurements or analyses performed on image data. The image data may be acquired by one or more different imaging modalities, including but not limited to, magnetic resonance (MR) imaging, computed tomography (CT), tomosynthesis, mammography, helical CT, x-ray, positron emission tomography (PET), PET-CT, fluoroscopy, ultrasound, single-photon emission computed tomography (SPECT), SPECT-CT, MR-PET, etc. Biomarkers may be detected in the image data to determine, for example, ejection fraction, wall mass or thickness, cardiac wall motion scoring, 17 segment perfusion model, fractional flow reserve, valve function, calcium score, machine encoding of stenosis grade, length, percentage or spatial distribution in coronary arteries, tumor morphology (e.g. margin characteristics such as smoothness, spiculation or texture), and other values.

Other types of diagnostic tests include, but are not limited to, laboratory or clinical tests (e.g., chemical tests to determine pH, blood count, lipids, troponin or other enzymes, blood sugar level, cholesterol level, presence or absence of genetic biomarkers) on a biological sample (e.g., blood, tissue, urine), physical examinations, investigations, questionings, monitoring of biological signals (e.g., electrocardiogram), medical procedures (e.g., colonoscopy), examination of radiology or cardiology reports, functional imaging (e.g., perfusion imaging, nuclear or metabolic imaging), computer-aided detection (CAD) and diagnosis based on medical images, and/or quantitative measurements based on medical data (e.g., images).

At 204, training unit 106 clusters the data into sub-datasets based on patient characteristics. This step may be optionally performed to improve the precision of learned classifiers (or predictors). Each cluster or sub-dataset represents patients who are more similar to each other with respect to one or more patient characteristics (i.e., share one or more common patient characteristics) than to those in other clusters or sub-datasets. Patient characteristics may include, but are not limited to, demographic attributes (e.g., age, gender, ethnicity or race), physical attributes (e.g., height, weight, genes), family history, habits, preexisting medical conditions (e.g., diseases, pathologies, allergies), temporary symptoms, test trajectories (or paths), patient management history (e.g., therapies, drug prescriptions), and so forth. Such patient characteristics may be derived from, for example, patient records or other available data. Exemplary clustering techniques include, but are not limited to, k-means clustering, density-based clustering, distribution-based clustering, genetic algorithms, principal component analysis, or other techniques capable of handling high-dimensional data.

At 206, training unit 106 applies a machine learning technique to train one or more classifiers for each sub-dataset to identify diagnostic test plans. By training one or more classifiers for each sub-dataset, the classifier may be tailored specifically for the sub-dataset (or cluster). It should also be appreciated, however, that the machine learning technique may also be applied to the entire training population without prior clustering to generate a general classifier.

Each diagnostic test plan identified by a classifier may include an optimal subset of diagnostic tests from the set of potential diagnostic tests D. The one or more classifiers may also be trained to determine an optimal sequence of the diagnostic tests in each of the diagnostic test plans to predict one or more medical conditions. The one or more classifiers may further be trained to prioritize the diagnostic tests in the subset. The diagnostic tests may be prioritized according to, for example, effectiveness of therapy, potential side-effects, cost, access to type of therapy (e.g., surgery may be the best therapy, but there are no organs available to transplant or there are already too many surgeries scheduled), or a combination thereof.

In addition, the one or more classifiers may also be trained to discover new relationships between patient characteristics that are presently not known but may influence clinical decision and patient management. The patient characteristics may be derived from the data representing the one or more sample patients. For example, the classifier may identify a relationship between different drug combinations that may be lethal for some patients (e.g., very young children). As another example, the classifier may identify a relationship between patients with particular patient characteristics (e.g., smoking or alcohol habits) with certain medical conditions.

The machine learning technique may be performed based on the data representing the one or more sample patients, diagnostic tests administered to the one or more sample patients, diagnostic test results and confirmed medical conditions associated with the administered diagnostic tests. The machine learning technique may include, but is not limited to, a decision tree, random forests, neural nets, non-linear or linear regression, and so forth. Many machine learning techniques are formulated as an optimization of an objective function (e.g., minimization of a cost function). The optimization function may seek to maximize information value (e.g., accuracy of test results relative to confirmed outcomes), while minimizing costs of the diagnostic test (e.g., time, expense, number of tests and/or risks of specific diagnostic tests). A joint cost function that combines weighted discrimination with different diagnostic test costs may be used in cost-sensitive machine learning algorithms.

The machine learning technique may take as input the results of measurements (or tests) having different accuracies relative to manual measurements, but provide more comprehensive and consistent coverage of the measurements over the entire image set and sample patient population. This is particularly useful when the imaging tests or measurements are performed retrospectively with image analysis algorithms in banked image data repositories, such as would be possible in a cloud medical image repository. The machine learning technique may also handle noisy input and output data, which makes it applicable to select lower cost tests with higher diagnostic sensitivity and specificity.

At 208, planning unit 107 applies the trained classifier from the training unit 106 to current patient data to generate a diagnostic test plan for a given patient. The given patient may be any individual that is currently undergoing examination or diagnosis for one or more medical conditions. The current patient data may include, for example, patient record or information derived therefrom (e.g., preexisting medical conditions, demographic attributes, physical attributes, family history, habits, preexisting medical conditions, temporary symptoms, patient management history, therapy outcomes, administered diagnostic test results). The diagnostic test plan may include an optimal sequence of diagnostic tests. The diagnostic tests in the diagnostic test plan may be prioritized according to, for example, effectiveness of therapy, side-effects, cost, access to type of therapy, or a combination thereof. A diagnosis may be determined based on results of the diagnostic tests in the diagnostic test plan.

In some implementations, an appropriate trained classifier is selected from the set of trained classifiers based on current patient characteristics extracted from the current patient data. As discussed previously, the trained classifier may be tailored specifically for data with one or more patient characteristics commonly shared within the sub-dataset (or cluster). The planning unit 107 may automatically select the classifier associated with the sub-dataset that best matches the current patient data (i.e., most similar patient characteristics).

The trained classifier may then be applied to the current patient data to identify diagnostic tests (or variables) from a set of possible diagnostic tests to generate a diagnostic test plan. The diagnostic test plan may include a composite diagnostic test sequence. Alternative subsets of diagnostic tests may be selected and combined in a hierarchical machine learning structure (e.g., decision tree or random forest) to predict one or more medical conditions.

Figure 3:
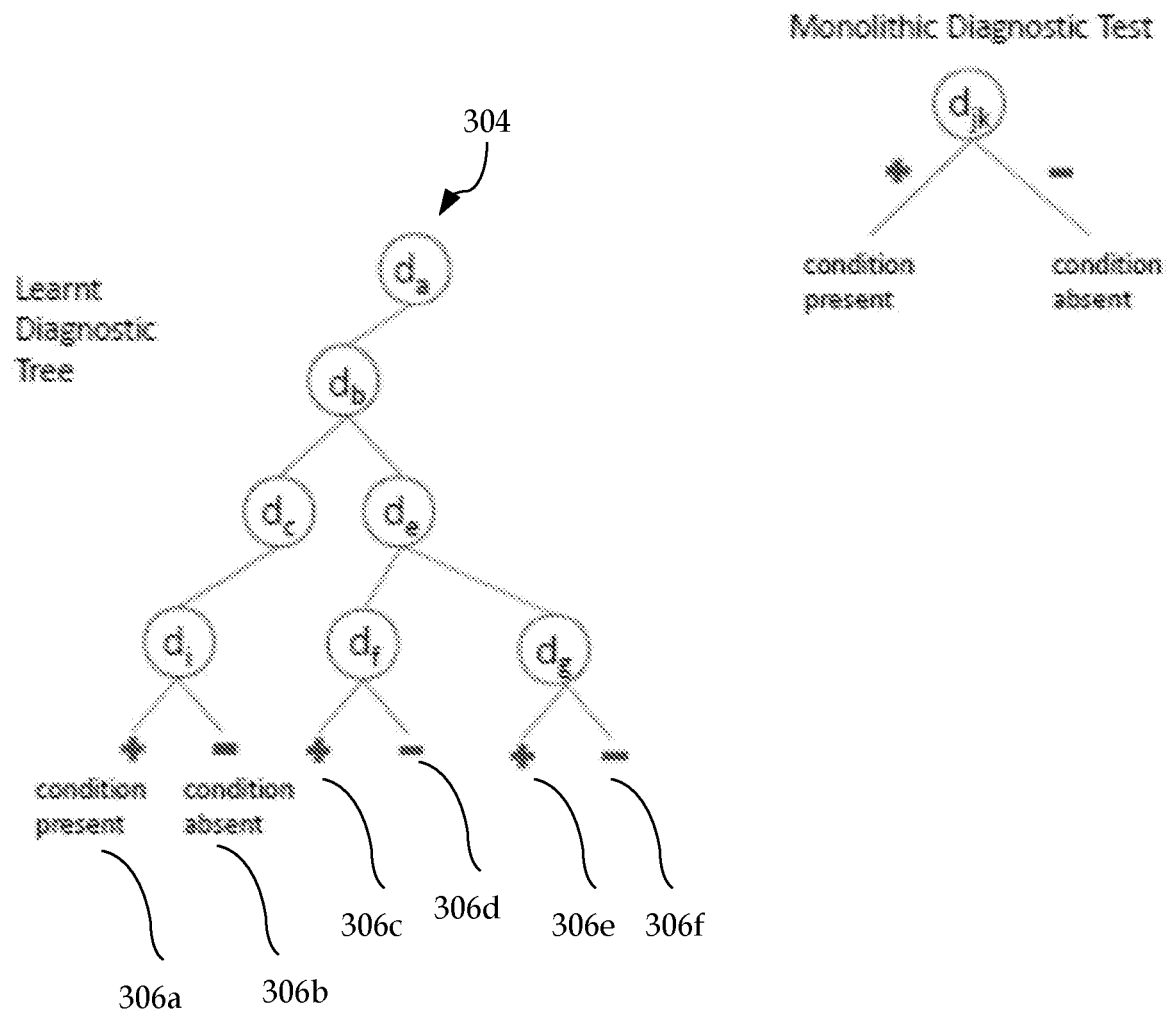
FIG. 3 illustrates an exemplary single monolithic test and an exemplary decision tree.

In some implementations, the trained classifier is a decision tree. FIG. 3 illustrates an exemplary single monolithic test $d_{jk}$ and an exemplary learned decision tree 304. The single monolithic test $d_{jk}$ determines if a specific medical condition is absent or present. The decision tree 304 is composed of internal nodes representing different diagnostic tests $d_a, \ldots, d_g$. Each branch from a node represents the outcome of the diagnostic test represented by that node. Each leaf node represents a class label (e.g., specific medical condition is absent or present). One or more diagnostic plans may be generated by determining one or more paths from the root ($d_a$) of the decision tree to a leaf node (306a-f). The leaf nodes 306a-f represent predictions that may be made based on the results of the combined diagnostic tests. The diagnostic plans generated by traversing the decision tree 304 may be sequential or parallel combinations of monolithic diagnostic tests.

The present framework may be applied to exploit existing combinations of tests already administered to the given patient, or to complete the cohort of tests through addition of a number of diagnostic tests to boost the diagnostic value of the cohort. More particularly, the decision tree 304 may be traversed based on existing results of one or more diagnostic tests that have been already been administered to the given patient, or new results from additional tests that are recommended by the planning unit 107.

The planning unit 107 may generate recommendations for diagnostic tests (e.g., via a user interface at workstation 103) while or after traversing the decision tree, depending on the availability of test results. For example, results of test $d_a$ may already be in the current patient data. After extracting the test results from the current patient data, planning unit 107 may traverse the decision tree 304 from $d_a$ to the next level node $d_b$, and generate a recommendation to administer test $d_b$. After test $d_b$ is performed, planning unit 107 may generate a recommendation (via a user interface) to administer either test $d_c$ or $d_e$ based on the test results of $d_b$. If the test results of $d_b$ is inconclusive, planning unit 107 may generate a recommendation to administer both neighboring tests $d_c$ and $d_e$. These tests $d_c$ and $d_e$ may be performed in parallel.

After administering one or more of the last level nodes ($d_i$, $d_f$, $d_g$), a prediction may be made based on the test results from one or more of the diagnostic tests $d_i$, $d_f$, $d_g$. In some implementations, the prediction is a binary decision (e.g., compared with a threshold value) that indicates whether a particular medical condition is present or absent based on a target sensitivity (or specificity) of the combined diagnostics. The prediction may also be a non-binary estimate of the probability of the medical condition of interest. It should be appreciated that other types of predictions may also be provided. The prediction may be presented via, for example, a user interface at workstation 103 to provide the user with decision support in diagnosing the medical conditions of interest.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A non-transitory computer readable medium embodying a program of instructions executable by machine to perform operations, the operations comprising:
   receiving data representing one or more sample patients, diagnostic tests administered to the one or more sample patients, diagnostic test results and confirmed medical conditions associated with the administered diagnostic tests;
   clustering the data into sub-datasets based on patient characteristics derived from the data, wherein each of the sub-datasets represents patients who are more similar to each other with respect to the patient characteristics than patients in other sub-datasets;
   training one or more classifiers for each of the sub-datasets to generate a set of classifiers for identifying diagnostic test plans;
   selecting, based on current patient data associated with a given patient, a classifier from the set of classifiers, wherein the selected classifier is associated with a sub-dataset that matches the current patient data, wherein the selected classifier comprises a decision tree with a root and internal nodes that represent diagnostic tests and leaf nodes that represent predictions, wherein the predictions are binary decisions that indicate whether a particular medical condition is present or absent based on a target sensitivity; and
   generating one or more diagnostic test plans for the given patient using the selected classifier, wherein the one or more diagnostic test plans include diagnostic tests of neighboring internal nodes within a same level of the selected classifier in response to inconclusive test results in the preceding level.

2. The non-transitory computer readable medium of claim 1, wherein the patient characteristics comprise demographic attributes, physical attributes, family history, habits, preexisting medical conditions, temporary symptoms, patient management history, or a combination thereof.

3. The non-transitory computer readable medium of claim 1, wherein the instructions are executable by the machine to train the set of classifiers to further determine an optimal sequence of the diagnostic tests in each of the diagnostic test plans.

4. The non-transitory computer readable medium of claim 1, wherein the instructions are executable by the machine to train the set of classifiers to discover new relationships between the patient characteristics derived from the data.

5. The non-transitory computer readable medium of claim 1, wherein at least one of the diagnostic test plans comprises a set of prioritized diagnostic tests.

6. The non-transitory computer readable medium of claim 1 wherein at least one of the diagnostic test plans comprises a set of diagnostic tests prioritized according to effectiveness of therapy, side-effects, cost, access to type of therapy, or a combination thereof.

7. A system for diagnostic test planning, comprising:
a non-transitory memory device for storing computer readable program code; and
a processor in communication with the memory device, the processor being operative with the computer readable program code to perform operations including
receiving data representing one or more sample patients, first diagnostic tests administered to the one or more sample patients, diagnostic test results and confirmed medical conditions associated with the administered first diagnostic tests,
training a set of classifiers based on the data to identify diagnostic test plans from the first diagnostic tests,
selecting, based on current patient data associated with a given patient, a classifier from the set of classifiers, wherein the selected classifier comprises a decision tree with a root and internal nodes that represent diagnostic tests and leaf nodes that represent predictions, wherein the predictions are binary decisions that indicate whether a particular medical condition is present or absent based on a target sensitivity, and
generating a diagnostic test plan by applying the selected classifier to the current patient data, wherein the diagnostic test plan comprises an optimal sequence of second diagnostic tests, wherein the diagnostic test plan includes the second diagnostic tests of neighboring internal nodes within a same level of the selected classifier in response to inconclusive test results in the preceding level.

8. The system of claim 7 wherein the first diagnostic tests are applied to a same sample patient over time.

9. The system of claim 7 wherein the first diagnostic tests comprise a measurement or analysis performed on image data.

10. The system of claim 9 wherein the image data is acquired by magnetic resonance (MR) imaging, computed tomography (CT), tomosynthesis, mammography, helical CT, x-ray, positron emission tomography (PET), PET-CT, fluoroscopy, ultrasound, single-photon emission computed tomography (SPECT), SPECT-CT, MR-PET, or a combination thereof.

11. The system of claim 9 wherein the measurement or analysis is performed to determine ejection fraction, wall mass or thickness, cardiac wall motion scoring, 17 segment perfusion model, fractional flow reserve, valve function, calcium score, machine encoding of stenosis grade, length, percentage or spatial distribution in coronary arteries, tumor morphology, or a combination thereof.

12. The system of claim 7 wherein the first diagnostic tests comprise a laboratory or clinical test on a biological sample, a physical examination, investigation, questioning, monitoring of a biological signal, a medical procedure, examination of a radiology or cardiology report, functional imaging, computer-aided detection based on medical images, quantitative measurement based on medical data, or a combination thereof.

13. The system of claim 7, wherein the processor is operative with the computer readable program code to train the set of classifiers by performing a machine learning technique that maximizes accuracy of test results relative to confirmed outcomes while minimizing costs of the first diagnostic tests.

14. The system of claim 7, wherein the processor is operative with the computer readable program code to apply the selected classifier by traversing the decision tree.

15. The system of claim 14 wherein the processor is further operative with the computer readable program code to present, via a user interface, one or more diagnostic test recommendations while or after traversing the decision tree.

16. The system of claim 7 wherein the processor is further operative with the computer readable program code to generate a prediction associated with a medical condition after applying the selected classifier.

17. The system of claim 7, wherein the optimal sequence of second diagnostic tests comprises prioritized second diagnostic tests.

18. The system of claim 7 wherein the optimal sequence of second diagnostic tests comprises a set of second diagnostic tests prioritized according to effectiveness of therapy, side-effects, cost, access to type of therapy, or a combination thereof.

19. The system of claim 7, wherein training the set of classifiers comprises training the set of classifiers to identify a new relationship between different drug combinations that are lethal for patients with one or more predetermined patient characteristics.

20. A method of diagnostic test planning, comprising:
receiving data representing one or more sample patients, first diagnostic tests administered to the one or more sample patients, diagnostic test results and confirmed medical conditions associated with the administered first diagnostic tests;
training a set of classifiers based on the data to identify diagnostic test plans;
selecting, based on current patient data associated with a given patient, a classifier from the set of classifiers, wherein the selected classifier comprises a decision tree with a root and internal nodes that represent diagnostic tests and leaf nodes that represent predictions, wherein the predictions are binary decisions that indicate whether a particular medical condition is present or absent based on a target sensitivity; and
generating a diagnostic test plan by applying the selected classifier to the current patient data, wherein the diagnostic test plan comprises an optimal sequence of second diagnostic tests, wherein the diagnostic test plan includes the second diagnostic tests of neighboring internal nodes within a same level of the selected classifier in response to inconclusive test results in the preceding level.

* * * * *